United States Patent
Truschel et al.

(10) Patent No.: US 10,682,478 B2
(45) Date of Patent: Jun. 16, 2020

(54) TRANSLATING RESPIRATORY THERAPY PARAMETERS

(71) Applicant: KONINKLIJKE PHILIPS N.V., Eindhoven (NL)

(72) Inventors: Anthony William Truschel, Oakmont, PA (US); Bryan Thomas Coles, Mars, PA (US)

(73) Assignee: Koninklijke Philips N.V., Eindhoven (NL)

(*) Notice: Subject to any disclaimer, the term of this patent is extended or adjusted under 35 U.S.C. 154(b) by 250 days.

(21) Appl. No.: 15/500,318

(22) PCT Filed: Aug. 3, 2015

(86) PCT No.: PCT/IB2015/055881
§ 371 (c)(1),
(2) Date: Jan. 30, 2017

(87) PCT Pub. No.: WO2016/020825
PCT Pub. Date: Feb. 11, 2016

(65) Prior Publication Data
US 2017/0216541 A1    Aug. 3, 2017

Related U.S. Application Data

(60) Provisional application No. 62/032,655, filed on Aug. 4, 2014.

(51) Int. Cl.
*A61M 16/00* (2006.01)
*G06F 19/00* (2018.01)
(Continued)

(52) U.S. Cl.
CPC .... *A61M 16/0051* (2013.01); *A61M 16/0069* (2014.02); *A61M 16/024* (2017.08);
(Continued)

(58) Field of Classification Search
CPC ............ A61M 16/0051; A61M 16/021; A61M 16/022; A61M 16/024; A61M 16/026;
(Continued)

(56) References Cited

U.S. PATENT DOCUMENTS

2007/0113186 A1   5/2007  Coles
2008/0004500 A1*  1/2008  Cazares ............... A61B 5/0031
                                                    600/300
(Continued)

FOREIGN PATENT DOCUMENTS

WO   WO2009023634 A2   2/2009
WO   WO2012168848 A1  12/2012

OTHER PUBLICATIONS

"Ventilator Calculator", Cruthu Services Medical, Dec. 3, 2013 https://play.google.com/store/apps/details?id=net.cruthu.ventcalc.

*Primary Examiner* — Nilay J Shah
(74) *Attorney, Agent, or Firm* — Daniel H. Brean

(57) ABSTRACT

A parameter translation system configured to determine respiratory therapy control parameters is provided. When a subject is prescribed respiratory therapy, his or her regimen will likely include receiving therapy from several different respiratory therapy devices. Respiratory therapy devices are often designed and/or approved for a niche depending on acuity of respiratory distress and/or insufficiency in the subject, the physical location of the subject, and/or other factors. These respiratory devices are made by a variety of manufacturers and deliver therapy with a variety of therapy regimes, settings, alarm parameters, and/or other control parameters. It is a laborious process to transfer such control parameters between two or more respiratory therapy devices. The present system facilitates translating these control parameters from one respiratory therapy device to another respiratory therapy device so the subject continues (Continued)

receiving the prescribed respiratory therapy when he or she switches from one device to another.

15 Claims, 3 Drawing Sheets

(51) Int. Cl.
*A61M 16/16* (2006.01)
*A61M 16/10* (2006.01)
*G16H 50/50* (2018.01)

(52) U.S. Cl.
CPC ....... *A61M 16/161* (2014.02); *G06F 19/3481* (2013.01); *A61M 2016/003* (2013.01); *A61M 2016/0027* (2013.01); *A61M 2016/0036* (2013.01); *A61M 2016/1025* (2013.01); *A61M 2205/3334* (2013.01); *A61M 2205/3368* (2013.01); *A61M 2205/3375* (2013.01); *A61M 2205/3379* (2013.01); *A61M 2205/3584* (2013.01); *A61M 2205/50* (2013.01); *G16H 50/50* (2018.01)

(58) Field of Classification Search
CPC .......... A61M 2205/50; A61M 2205/52; A61M 2205/60
See application file for complete search history.

(56) References Cited

U.S. PATENT DOCUMENTS

| | | |
|---|---|---|
| 2009/0020120 A1* | 1/2009 | Schatzl .................. A61B 5/087 128/204.22 |
| 2010/0078017 A1 | 4/2010 | Andrieux |
| 2010/0138236 A1 | 6/2010 | Rappaport |
| 2011/0152830 A1 | 6/2011 | Ruchti |
| 2013/0104894 A1 | 5/2013 | Steinhauer |
| 2013/0199534 A1* | 8/2013 | Steinhauer ........ A61M 16/0057 128/204.23 |

* cited by examiner

TRANSLATING RESPIRATORY THERAPY PARAMETERS

CROSS-REFERENCE TO RELATED APPLICATIONS

This patent application claims the priority benefit under 35 U.S.C. § 371 of international patent application no. PCT/IB2015/055881, filed Aug. 3, 2015, which claims the priority benefit under 35 U.S.C. § 119(e) of U.S. Provisional Application No. 62/032,655 filed on Aug. 4, 2014, the contents of which are herein incorporated by reference.

BACKGROUND OF THE INVENTION

1. Field of the Invention

The present disclosure pertains to a parameter translation system configured to determine respiratory therapy control parameters.

2. Description of the Related Art

It is well known to provide respiratory therapy to the airway of a patient. Common respiratory therapy includes ventilation (invasive and non-invasive), positive airway pressure support, continuous positive airway pressure support, bi-level support, proportional assist ventilation, and/or other types of respiratory therapy. A wide range of respiratory therapy device models from various manufacturers are used to provide respiratory therapy. An individual respiratory therapy device controls respiratory therapy based on control parameters unique to the type of respiratory therapy, the respiratory therapy device model, and the manufacturer. Switching from a respiratory therapy device of a first model to a respiratory therapy device of a second model can be difficult for some patients. A respiratory therapy prescription generated for a respiratory therapy device of a first model does not typically apply to a respiratory therapy device of a second model.

SUMMARY OF THE INVENTION

Accordingly, one or more aspects of the present disclosure relate to a parameter translation system configured to determine respiratory therapy control parameters. The system comprises one or more physical computer processors, and/or other components. The one or more physical computer processors are configured, by computer readable instructions, to receive a prescribed respiratory therapy for a subject that defines a pressurized flow of breathable gas to be delivered to the subject by a first respiratory therapy device model. The prescribed respiratory therapy includes an identification of a first respiratory therapy regime type and values for a first set of control parameters associated with the first therapy regime type. The one or more physical computer processors are configured to obtain a second respiratory therapy device model and determine an alternative mode of delivery of the prescribed respiratory therapy to be delivered to the subject by a second respiratory therapy device model. The second respiratory therapy device model is different from the first respiratory therapy device model.

The determination includes determination of an identification of a second respiratory therapy regime type different from the first respiratory therapy regime type, with regard to the values and/or information for a second set of control parameters associated with the second therapy regime type, wherein the second set of control parameters is different from the first set of control parameters. The second therapy regime type may be determined to be substantially equivalent to and/or sufficiently effective relative to the first therapy regime. The one or more physical computer processors are configured to effectuate communication of the identification of the second respiratory therapy regime type and the values for the second set of control parameters for implementation on a respiratory therapy device of the second respiratory therapy device model.

Yet another aspect of the present disclosure relates to a method for determining respiratory therapy control parameters with a parameter translation system. The system comprises one or more physical computer processors, and/or other components. The method comprises receiving, with the one or more physical computer processors, a prescribed respiratory therapy for a subject that defines a pressurized flow of breathable gas to be delivered to the subject by a first respiratory therapy device model, the prescribed respiratory therapy including an identification of a first respiratory therapy regime type and values for a first set of control parameters associated with the first therapy regime type; obtaining, with the one or more physical computer processors, a second respiratory therapy device model; and determining, with the one or more physical computer processors, an alternative mode of delivery of the prescribed respiratory therapy to be delivered to the subject by a second respiratory therapy device model different from the first respiratory therapy device model. Such determination includes determination of an identification of a second respiratory therapy regime type and values for a second set of control parameters associated with the second therapy regime type. The second therapy regime may be substantially equivalent to and/or sufficiently effective relative to the first therapy regime. The second set of control parameters is different from the first set of control parameters. The method further comprising effectuating, with the one or more physical computer processors, communication of the identification of the second respiratory therapy regime type and the values for the second set of control parameters for implementation on a respiratory therapy device of the second respiratory therapy device model.

Still another aspect of the present disclosure relates to a system configured to determine respiratory therapy control parameters. The system comprises means for receiving a prescribed respiratory therapy for a subject that defines a pressurized flow of breathable gas to be delivered to the subject by a first respiratory therapy device model, the prescribed respiratory therapy including an identification of a first respiratory therapy regime type and values for a first set of control parameters associated with the first therapy regime type; means for obtaining a second respiratory therapy device model; and means for determining an alternative mode of delivery of the prescribed respiratory therapy to be delivered to the subject by a second respiratory therapy device model different from the first respiratory therapy device model. Such determination includes determination of an identification of a second respiratory therapy regime type different from the first respiratory therapy regime type, and values for a second set of control parameters associated with the second therapy regime type. The second set of control parameters is different from the first set of control parameters. The second therapy regime may be substantially equivalent to and/or sufficiently effective relative to the first therapy regime. The system further comprising means for effectuating communication of the identification of the second respiratory therapy regime type and the values for the second set of control parameters for implementation on a respiratory therapy device of the second respiratory therapy device model.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

BRIEF DESCRIPTION OF THE DRAWINGS

FIG. 2 illustrates a second embodiment of the parameter translation system; and.

DETAILED DESCRIPTION OF EXEMPLARY EMBODIMENTS

Figure 1:
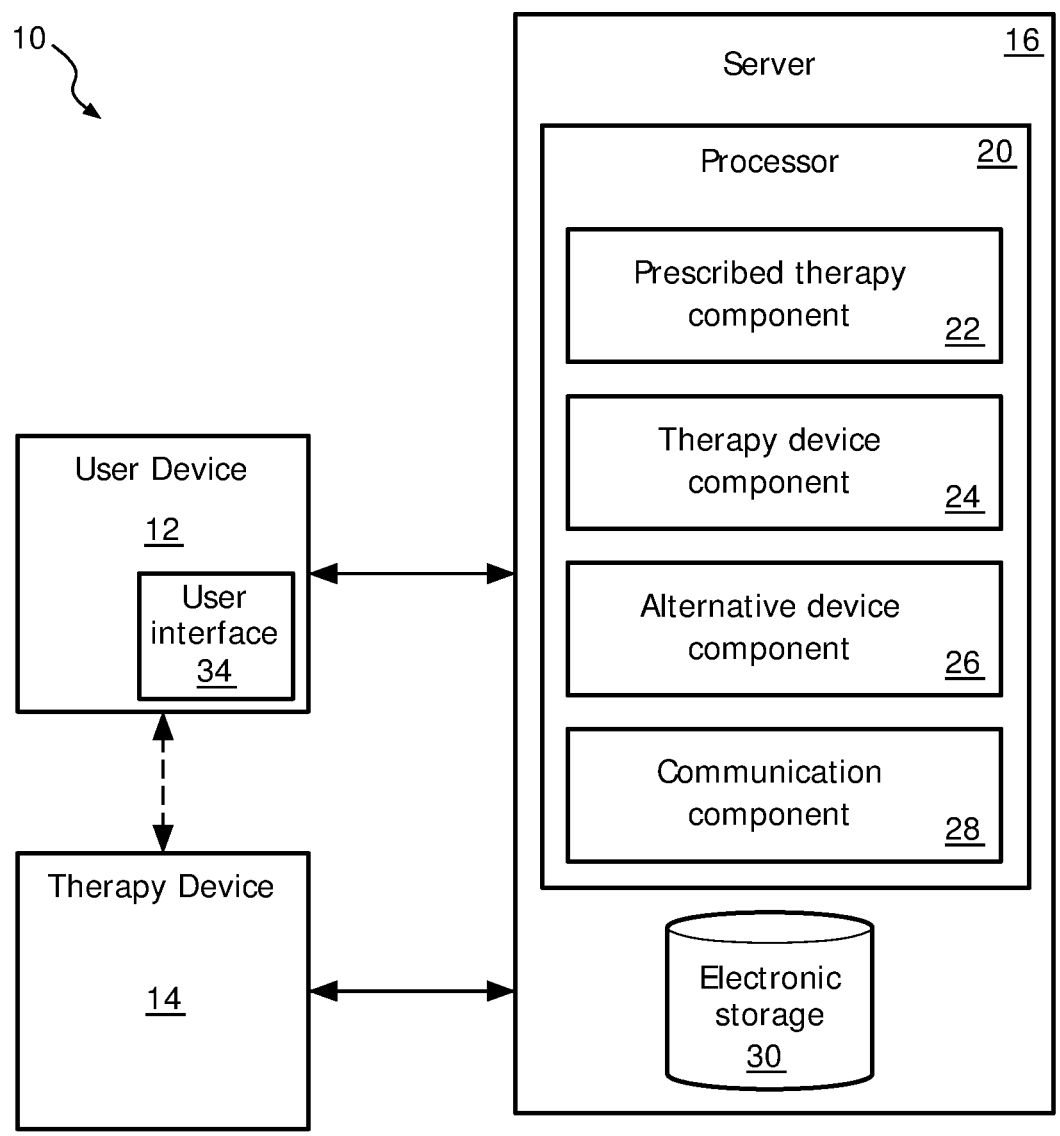
FIG. 1 illustrates a parameter translation system configured to determine respiratory therapy control parameters.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality. Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a parameter translation system 10 configured to determine respiratory therapy control parameters. In some embodiments, system 10 includes one or more of a processor 20, electronic storage 30, and/or other components. In some embodiments, processor 20, electronic storage 30, and/or other components are included in a server 16. Server 16 is configured to communicate with one or more user devices 12, one or more therapy devices 14, and/or other devices.

When a subject is prescribed respiratory therapy, his or her regimen will likely include receiving therapy from several different respiratory therapy devices (e.g., one or more devices at a doctor's office and/or hospital, one or more devices at home, one or more devices used in an ambulatory setting, etc.). Respiratory therapy devices are often designed and/or approved for a niche depending on acuity of respiratory distress and/or insufficiency in the subject, the physical location of the subject, and/or other factors. There are respiratory therapy devices designed for the ICU, respiratory therapy devices designed to work in ambulatory settings for subject transport, respiratory therapy devices that are designed for continuous use in the subject's home, and/or other respiratory devices.

These respiratory devices are made oftentimes from a variety of manufacturers and deliver therapy with a variety of therapy regimes, settings, alarm parameters, and/or other control parameters. It is a laborious process to transfer such control parameters between two or more respiratory therapy devices, even devices that are manufactured by the same manufacturer. System 10 facilitates translating these control parameters from one respiratory therapy device to another respiratory therapy device so the subject continues receiving the prescribed respiratory therapy when he or she switches from one device to another. For example, system 10 is configured to take a respiratory therapy prescription generated in one manufacturer's terms and translate it to a substantially therapeutically equivalent prescription in another manufacturer's terms. The present invention also contemplates translating the control parameters from one respiratory therapy device to another identical respiratory therapy device of the same manufacturer/model.

System 10 is configured to receive a prescribed respiratory therapy for a subject that defines a pressurized flow of breathable gas to be delivered to the subject by a first respiratory therapy device model. The first respiratory therapy device model may be identifiable based on the manufacturer, model number, model name, serial number, and/or other identifying characteristics. In some embodiments, the prescribed therapy is uploaded to system 10 by a doctor, a caregiver, the subject, and/or other users via a user device 12 (described below), for example. The first respiratory therapy device model may be a model that a doctor typically works with, a model the subject uses at home, and/or other models, for example. The prescribed respiratory therapy includes an identification of a first respiratory therapy regime type (e.g., ventilation, a type of ventilation, etc.) and values for a first set of control parameters (e.g., therapy set points, gas parameters, breathing parameters, alarm set points) associated with the first therapy regime type.

System 10 is configured to obtain a second respiratory therapy device model and determine an alternative mode of delivery of the prescribed respiratory therapy to the subject by the second respiratory therapy device model. The second respiratory therapy device model may be the model of a therapy device that a subject plans to receive therapy from. For example, therapy device 14 may be a therapy device of the second respiratory therapy device model. Therapy device 14 may be made by a different manufacturer than the manufacturer of the first therapy device model, and/or therapy device 14 may be another model of therapy device made by the same manufacturer, for example. By way of a non-limiting example, the first respiratory therapy device model may be a model of respiratory therapy device that a doctor typically works with and the second respiratory therapy device model may be a model of the respiratory therapy device a subject has at home.

Determining the alternative mode of delivery of the prescribed respiratory therapy by the second respiratory therapy device includes identification of a second respiratory therapy regime type that has a different set of control parameters and/or other information associated with the second therapy regime type, but has been determined to be therapeutically equivalent and/or sufficiently effective. In some embodiments, the second therapy regime is different from the first respiratory therapy regime type but achieves the same and/or similar therapeutic results in a subject relative to the first respiratory therapy regime. Determining the alternative mode of delivery of the prescribed respiratory therapy by the second respiratory therapy device includes identification of values for a second set of control parameters associated with the second therapy regime type, and/or other information. For example, system 10 is configured to determine the alternative mode of delivery such that the subject receives respiratory therapy (based on the received prescription) from the therapy device of the second therapy device model (e.g., therapy device 14) according to a set of control parameters (e.g., a second set) determined for implementation on the second therapy device model. The respiratory therapy (e.g., the second therapy regime type) received from the device of the second therapy model with the second set of control parameters achieves the same and/or similar therapeutic results in a subject relative to the first respiratory therapy regime.

System 10 is configured to effectuate communication of the second respiratory therapy regime type and the values for the second set of control parameters for implementation on a respiratory therapy device of the second respiratory therapy device model (e.g., therapy device 14). In some embodiments, system 10 is configured to effectuate communication directly to a therapy device of the second respiratory therapy device model (e.g., therapy device 14). In some embodiments, system 10 is configured to effectuate communication to a user device 12. System 10 may be configured to effectuate communication back to the user device 12 from which it received the original prescribed respiratory therapy, and/or system 10 may effectuate communication to other user devices 12.

Therapy device 14 is configured to deliver respiratory therapy to a subject. Therapy device 14 has a specific respiratory therapy device model. The model may indicate the manufacturer of therapy device 14, one or more respiratory therapy regime types provided by therapy device 14, and/or other characteristics of therapy device 14. In some embodiments, therapy device 14 is configured to provide pressure controlled (e.g., constant and/or volume targeted) respiratory therapy, volume and/or flow controlled respiratory therapy, proportional assist respiratory therapy, and/or other respiratory therapy.

In some embodiments, therapy device 14 is and/or includes a pressure generator configured to generate a pressurized flow of breathable gas for delivery to an airway of a subject. Therapy device 14 may control one or more parameters of the flow of gas (e.g., flow rate, pressure, volume, temperature, gas composition, timing, etc.) for therapeutic purposes, and/or for other purposes. By way of a non-limiting example, therapy device 14 may be configured to control the flow rate and/or pressure of the flow of gas to provide ventilation support to the airway of a subject.

In some embodiments, therapy device 14 receives a flow of gas from a gas source, such as the ambient atmosphere, and elevates the pressure of that gas for delivery to the airway of a subject. Therapy device 14 is and/or includes any device, such as, for example, a pump, blower, piston, or bellows, that is capable of elevating the pressure of gas for delivery to a subject. The present disclosure also contemplates that gas other than ambient atmospheric air may be delivered to a subject. In such embodiments, a pressurized canister or tank of gas containing air, oxygen, and/or another gas may supply an intake of therapy device 14. In some embodiments, therapy device 14 includes a blower that is driven at a substantially constant speed during the course of respiratory therapy to provide the pressurized flow of breathable gas with a substantially constant elevated pressure and/or flow rate. Therapy device 14 may comprise one or more valves for controlling the pressure/flow of gas. The present disclosure also contemplates controlling the operating speed of the blower, either alone or in combination with such a valve, to control the pressure/flow of gas provided to the subject.

In some embodiments, therapy device 14 includes a subject interface configured to deliver the pressurized flow of breathable gas to a subject. The subject interface may include one or more of a conduit configured to conduct the pressurized flow of breathable gas, an interface appliance configured to interface with the airway of the subject, and/or other components.

User device 12 is configured such that a user (e.g., a subject, a doctor, a caregiver) may access system 10 via user device 12. In some embodiments, user device 12 is configured to communicate with server 16, therapy device 14, and/or other components according to a peer-to-peer architecture, a client/server architecture, and/or other architectures. An individual user device 12 may be associated with an individual doctor, caregiver, subject, and/or other users, for example. User device 12 may include communication lines, or ports to enable the exchange of information with a network, other computing platforms (e.g., one or more other user devices 12, server 16, therapy device 14), and/or other devices. In some embodiments, communication between user device 12, server 16, therapy device 14, and/or other components associated with system 10 may be wireless and/or via wires. For example, user device 12 may communicate with server 16 and/or therapy device 14 wirelessly via the internet, a Wi-Fi network, via Bluetooth® technology, and/or other wireless technology. In some embodiments, user device 12 may communicate with therapy device 14 via a wired USB connection, for example. By way of non-limiting example, user device 12 may include one or more of a desktop computer, a laptop computer, a handheld computer, a tablet computing platform, a NetBook, a smart-phone, and/or other computing platforms.

In some embodiments, user device 12 includes a user interface 34 and/or other components. User interface 34 is configured to provide an interface between system 10 and a subject and/or other users (e.g., a doctor, care-giver, etc.) through which the subject and/or other users may provide information to and receive information from system 10. This enables data, cues, results, and/or instructions and any other communicable items, collectively referred to as "information," to be communicated between subject 12 and one or more of server 16, processor 20, electronic storage 30, therapy device 14, and/or other components of system 10. This may allow a doctor, a caregiver, a subject, and/or other users to provide a prescribed therapy to system 10 (e.g., via text, email, entry and/or selection of information through user interface 34), receive a communication of the identification of a second respiratory therapy regime type and values for a second set of control parameters for implementation on a respiratory therapy device of a second respiratory therapy device model from system 10, and/or communicate in other ways with system 10, for example.

Examples of interface devices suitable for inclusion in user interface 34 comprise a keypad, buttons, switches, a keyboard, knobs, levers, a display screen, a touch screen, speakers, a microphone, an indicator light, an audible alarm, a printer, a tactile feedback device, and/or other interface devices. It is to be understood that other communication techniques, either hard-wired or wireless, are also contemplated by the present disclosure as user interface 34. For example, the present disclosure contemplates that user interface 34 may be integrated with a removable storage interface provided as part of user device 12. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 34 comprise, but are not limited to, an RS-232 port, RF link, an IR link, modem (telephone, cable or other). In short, any technique for communicating information with system 10 is contemplated by the present disclosure as user interface 34.

In some embodiments, user interface 34 comprises a plurality of separate interfaces. In some embodiments, user interface 34 comprises at least one interface that is provided integrally with user device 12. For example, user interface 34 may be and/or include a graphical user interface that is presented to a subject on a user device 12 (e.g., a smartphone and/or other computing device associated with subject, doctor, caregiver, etc.).

Figure 2:
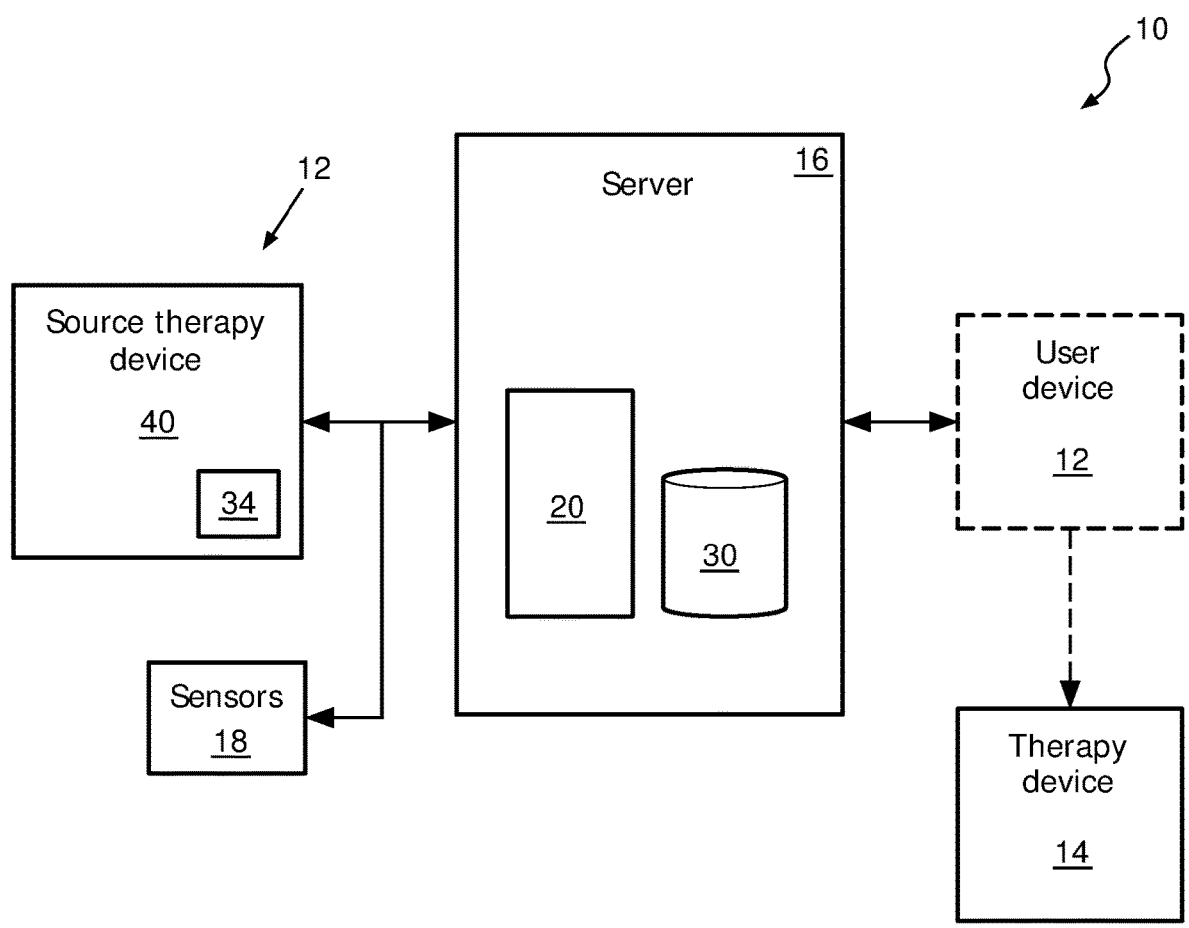

As shown in FIG. 2, user device 12 may be and/or include a source therapy device 40, one or more sensors 18, and/or other devices. In some embodiments, such as when user device 12 is a smartphone associated with a user, the smartphone, source therapy device 40, and/or sensors 18 may be separate devices.

Source therapy device 40 is similar to therapy device 14 but is a respiratory therapy device of a different model. For example, the model of source therapy device 40 may be the first respiratory therapy device model described above. Like therapy device 14, source therapy device 40 is configured to provide pressure controlled (e.g., constant and/or volume targeted) respiratory therapy, volume and/or flow controlled respiratory therapy, proportional assist respiratory therapy, and/or other respiratory therapy to a subject. Source therapy device may include the same and/or similar components as therapy device 14 (described above). In some embodiments, source therapy device 40 includes user interface 34.

In some embodiments, source therapy device 40 is configured to communicate directly with server 16. In some embodiments, source therapy device 40 is configured to communicate information that conveys the prescribed respiratory therapy for a subject that defines the pressurized flow of breathable gas to be delivered to the subject by the first respiratory therapy device model (e.g., source therapy device 40). The communicated information includes an identification of the first respiratory therapy regime type and values for the first set of control parameters (e.g., therapy set points, gas parameters, breathing parameters, alarm set points) associated with the first therapy regime type, and/or other information.

Sensor 18 is configured to generate output signals conveying information related to a pressurized flow of breathable gas delivered to the subject by a respiratory therapy device of the first respiratory therapy device model (e.g., source therapy device 40) and/or other information. The information related to the pressurized flow of breathable gas may include information related to one or more parameters of the pressurized flow of breathable gas. Information related to one or more parameters of the pressurized flow of breathable gas may include information related to a flow rate, a volume, a pressure, humidity, temperature, acceleration, velocity, and/or other gas parameters; breathing parameters related to the respiration of the subject such as a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other breathing parameters; parameters related to the operation of the respiratory therapy device of the first respiratory therapy device model (e.g., source therapy device 40), and/or other components of system 10; parameters related to the ambient environment, and/or other information.

Sensor 18 may comprise one or more sensors that measure such parameters directly (e.g., through communication with the pressurized flow of breathable gas in a conduit of a subject interface delivering the gas to the subject). Sensor 18 may comprise one or more sensors that generate output signals related to the pressurized flow of breathable gas indirectly. For example, sensor 18 may comprise one or more sensors configured to generate an output based on an operating parameter of source therapy device 40 (e.g., a current drawn, voltage, and/or other operating parameters), and/or other sensors.

Sensor 18 may include pressure sensors, flow rate sensors, volume sensors, humidity sensors, liquid level sensors, usage time sensors, temperature sensors, acoustic sensors configured to generate information related to the respiration of a subject, an Oxygen sensor to determine the existence of oxygen therapy, and/or other sensors. Sensor 18 may include a plurality of individual sensors located at various locations in and/or in proximity to source therapy device 40, the subject, and/or other locations. FIG. 2 illustrates sensor 18 as a separate component in proximity to source therapy device 40. This is not intended to be limiting. Any number of sensors 18 may be located anywhere within system 10 (including within source therapy device 40) provided system 10 functions as described herein.

In some embodiments, sensor 18 may be fixedly coupled with therapy device 14, and/or other therapy devices. In some embodiments, sensor 18 is portable. In some embodiments, sensor 18 may be one or more aftermarket sensors manufactured by a manufacturer that is the same as and/or different than the manufacturer of a therapy device (e.g., therapy device 14). In some embodiments, sensor 18 may be configured to generate output signals conveying information related to the pressurized flow of breathable gas delivered to the subject by a source therapy device (e.g., a respiratory therapy device of the first respiratory therapy device model such as source therapy device 40), and/or other information so that the subject may be converted from using the source therapy device to another device (e.g., a respiratory therapy device of the second therapy device model such as therapy device 14). In some embodiments, sensor 18 may be configured to generate output signals conveying information related to the pressurized flow of breathable gas delivered to the subject by a source therapy device without cooperation from the source therapy device.

In some embodiments, sensor 18 is configured to communicate directly with server 16. In some embodiments, sensor 18 is configured to communicate output signals that convey information related to the prescribed respiratory therapy for a subject that defines the pressurized flow of breathable gas to be delivered to the subject by the first respiratory therapy device model (e.g., source therapy device 40). The communicated information includes information related to an identification of the first respiratory therapy regime type and values for the first set of control parameters (e.g., therapy set points, gas parameters, breathing parameters, alarm set points) associated with the first therapy regime type, and/or other information.

Returning to FIG. 1, server 16 is configured to communicate with one or more client computing platforms (e.g., user device 12, therapy device 14) according to client server architecture and/or other architectures. In some embodiments, server 16, user device 12, therapy device 14, and/or other devices may be operatively linked via one or more electronic communication links. For example, such electronic communication links may be established, at least in part, via a network such as the internet and/or other networks. It will be appreciated that this is not intended to be limiting, and that the scope of this disclosure includes embodiments in which server 16, user device 12, therapy device 14, and/or other devices may be operatively linked via some other communication media.

Server 16 may include communication lines, or ports to enable the exchange of information with a network and/or other computing platforms. Illustration of server 16 in FIG. 1 is not intended to be limiting. Server 16 may include a plurality of hardware, software, and/or firmware components operating together to provide the functionality attributed herein to server 16. For example, server 16 may be implemented by a cloud of computing platforms operating together as server 16. Server 16 may comprise processor 20, electronic storage 30, and/or other components.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., server 16, user device 12, therapy device 14), or processor 20 may represent processing functionality of a plurality of devices operating in coordination.

As shown in FIG. 1, processor 20 is configured to execute one or more computer program components. The one or more computer program components may include one or more of a prescribed therapy component 22, a therapy device component 24, an alternative determination component 26, a communication component 28, and/or other components. Processor 20 may be configured to execute components 22, 24, 26, and/or 28 by software; hardware; firmware; some combination of software, hardware, and/or firmware; and/or other mechanisms for configuring processing capabilities on processor 20.

It should be appreciated that although components 22, 24, 26, and 28 are illustrated in FIG. 1 as being co-located within a single processing unit, in embodiments in which processor 20 includes multiple processing units, one or more of components 22, 24, 26, and/or 28 may be located remotely from the other components. The description of the functionality provided by the different components 22, 24, 26, and/or 28 described below is for illustrative purposes, and is not intended to be limiting, as any of components 22, 24, 26, and/or 28 may provide more or less functionality than is described. For example, one or more of components 22, 24, 26, and/or 28 may be eliminated, and some or all of its functionality may be provided by other components 22, 24, 26, and/or 28. As another example, processor 20 may be configured to execute one or more additional components that may perform some or all of the functionality attributed below to one of components 22, 24, 26, and/or 28.

Prescribed therapy component 22 is configured to receive a prescribed respiratory therapy for a subject. In some embodiments, prescribed therapy component 22 is configured to receive the prescribed respiratory therapy wirelessly via a network such as the internet and/or other networks. Prescribed therapy component 22 is configured to receive the prescribed therapy from a user device 12 (e.g., via user interface 34), a source therapy device 40 (FIG. 2), and/or from other sources. In some embodiments, the prescribed therapy is uploaded to system 10 by a doctor, a caregiver, the subject, and/or other users via a user device 12 for example. Uploading may refer to emailing, texting, manually entering and/or selecting information, saving an electronic file on server 16, and/or other communication of information. In some embodiments, prescribed therapy component 22 is configured to determine a prescribed therapy based on output signals from sensor 18 (FIG. 2). As described above, the output signals from sensor 18 convey information related to an identification of the first respiratory therapy regime type and values for the first set of control parameters (e.g., therapy set points, gas parameters, breathing parameters, alarm set points) associated with the first therapy regime type, and/or other information.

The prescribed therapy defines a pressurized flow of breathable gas to be delivered to the subject by a first respiratory therapy device model (e.g., the model of source therapy device 40 shown in FIG. 2). A respiratory therapy device model may be associated with a manufacturer, a model number, a model name, a serial number, possible therapy regime types delivered by the respiratory therapy device, and/or other characteristics of a respiratory therapy device. For example, the first respiratory therapy device model may be a model that a doctor typically works with, a model the subject uses at home, and/or other models, for example.

The prescribed respiratory therapy includes an identification of a first respiratory therapy regime type, values for a first set of control parameters associated with the first therapy regime type, and/or other information. Values for the first set of control parameters associated with the first therapy regime type include values for one or more parameters such as a flow rate, a volume, a pressure, humidity, temperature, acceleration, velocity, and/or other gas parameters; breathing parameters related to the respiration of the subject such as a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other breathing parameters; parameters related to the operation of the respiratory therapy device of the first respiratory therapy device model (e.g., source therapy device 40), and/or other components of system 10; parameters related to the ambient environment, and/or other information.

Therapy device component 24 is configured to obtain a second respiratory therapy device model. Therapy device component 24 is configured to obtain the second therapy device model via information entered and/or selected by a subject, doctor, caregiver, and/or other users through user interface 34, information stored in electronic storage 30 (e.g., previously stored information that indicates the model of a respiratory therapy device owned by a subject), information received from the second respiratory therapy device (e.g., therapy device 14 may communicate information related to its presence, availability, and/or model), and/or from other sources. The second respiratory therapy device model may be the model of a therapy device that a subject plans to receive therapy from. For example, therapy device 14 may be a therapy device of the second respiratory therapy device model. Therapy device 14 may be made by a different manufacturer than the manufacturer of the first therapy device model (e.g., source therapy device 40), and/or therapy device 14 may be another model of therapy device made by the same manufacturer, for example.

Alternative therapy determination component 26 is configured to determine an alternative mode of delivery of the prescribed respiratory therapy to be delivered to the subject by a second respiratory therapy device model (e.g., the model of therapy device 14). The determination includes determination of an identification of a second respiratory therapy regime type, values for a second set of control parameters associated with the second therapy regime type, and/or other information. Determining the alternative mode of delivery of the prescribed respiratory therapy by the second respiratory therapy device includes identification of a second respiratory therapy regime type that has a different set of control parameters and/or other information associated with the second therapy regime type, but has been determined to be therapeutically equivalent and/or sufficiently effective. In some embodiments, the second therapy regime is different from the first respiratory therapy regime type but achieves the same and/or similar therapeutic results in a subject relative to the first respiratory therapy regime.

For example, a patient may be using a LTV1200 Ventilator from CareFusion in NPPV mode at home, with the PEEP setting of 4 cm H20, the Pressure Support Setting of 20 cm H20, rise rate setting of 4, sensitivity setting of 2. These settings are the source therapy device mode and control parameters. If the patient is transferred to a skilled nursing facility in which the staff is only comfortable with a Philips device, therapy device for the second respiratory therapy may be a Philips Trilogy 100, the mode setting would be determined by the invention to be S mode, with IPAP setting 20, EPAP setting 4, rise rate setting of 1, and Flow Trigger selected with trigger sensitivity 2 for sufficiently effective therapy.

Alternative therapy determination component 26 is configured such that the second set of control parameters is different from the first set of control parameters. Differences may include different values for the same and/or similar parameters, additional parameters needed to control the second respiratory therapy device model (that are not needed to control the first model), fewer parameters needed to control the second respiratory therapy device model (that are needed to control the first model), and/or altogether different parameters that are used to control the respiratory therapy device of the second respiratory therapy device model (e.g., therapy device 14). For example, the first set of control parameters may include one or more of an inhalation pressure parameter and an exhalation pressure parameter. The second set of control parameters may include an inhalation pressure parameter that has a different value, an exhalation pressure parameter that has a different value, a timing parameter, and a breath rate parameter.

In some embodiments, alternative therapy determination component 26 is configured to determine the alternative mode of delivery of the prescribed respiratory therapy, including the determination of the identification of the second respiratory therapy regime type and the values for the second set of control parameters, to be delivered to the subject by the second respiratory therapy device model based on one or more sources of information. Alternative therapy determination component 26 is configured to determine the alternative mode of delivery based on the received prescribed respiratory therapy, information determined by prescribed therapy component 22, the obtained second respiratory therapy device model, information received from source therapy device 40 (FIG. 2), the output signals from sensor 18 (FIG. 2), information stored in electronic storage 30, and/or other information.

For example, in some embodiments, electronic storage 30 may be an/or include a translation database configured to electronically store information related to the first respiratory therapy device model, the first respiratory therapy regime type, and the values for the first set of control parameters associated with the first therapy regime type; information related to the second respiratory therapy device model, the second respiratory therapy regime type and the values for the second set of control parameters associated with the second therapy regime type; translation information, and/or other information. In some embodiments, the translation information defines relationships between one or more of the first respiratory therapy device model, the first respiratory therapy regime type, and/or the values for the first set of control parameters associated with the first therapy regime type, and one or more of the second respiratory therapy device model, the second respiratory therapy regime type, and/or the values for the second set of control parameters associated with the second therapy regime type. In some embodiments, alternative determination component 26 is configured to determine the alternative mode of delivery of the prescribed respiratory therapy to be delivered to the subject by the second respiratory therapy device model based at least in part on the translation information.

By way of a non-limiting example, the database may indicate that the therapy is designed to deliver one type of breath when triggered by a patient's inspiratory effort and another type of breath when the machine initiates a breath as indicated by the relative phasing of the pressure and flow signals. The interval of mechanical breaths may be determined based on an analysis of the database during apneac periods, and/or other information. The levels of pressure and/or flow may be determined from the database based on the catalog of breaths in the database, for example.

In some embodiments, alternative determination component 26 is configured such that the translation information is updatable. For example, a user, via user interface 34 of user device 12, may update translation information that defines relationship information for values for a first set of control parameters associated with a first therapy regime type and values for a second set of control parameters associated with a second therapy regime type. For example, if the second therapy device allows for an additional feature not available on the first therapy device but desirable and familiar to the doctor administering the therapy with the second device such as leak compensation or a programmable sigh feature. The control parameters may be adjusted to include these additional features along with the automatic translation.

Communication component 28 is configured to effectuate communication of the identification of the second respiratory therapy regime type, the values for the second set of control parameters, and/or other information for implementation on a respiratory therapy device of the second respiratory therapy device model (e.g., therapy device 14). In some embodiments, communication component 28 is configured to effectuate communication directly to a therapy device of the second respiratory therapy device model (e.g., therapy device 14) as shown in FIG. 1. In some embodiments, system 10 is configured to effectuate communication to a user device 12 and then to therapy device 14 (as shown by the dotted lines in FIG. 1 and FIG. 2). System 10 may be configured to effectuate communication back to the user device 12 from which it received the original prescribed respiratory therapy (FIG. 1), and/or system 10 may effectuate communication to other user devices 12 (FIG. 2). In some embodiments, communication component 28 is configured to effectuate communication wirelessly and/or via wires.

Electronic storage 30 comprises electronic storage media that electronically stores information. The electronic storage media of electronic storage 30 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 30 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 30 may store software algorithms, information determined by processor 20, information received via user device 12, and/or other information that enables system 10 to function properly. Electronic storage 30 may be (in whole or in part) a separate component within system 10, or electronic storage 30 may be provided (in whole or in part) integrally with one or more other components of system 10 (e.g., server 16).

Figure 3:
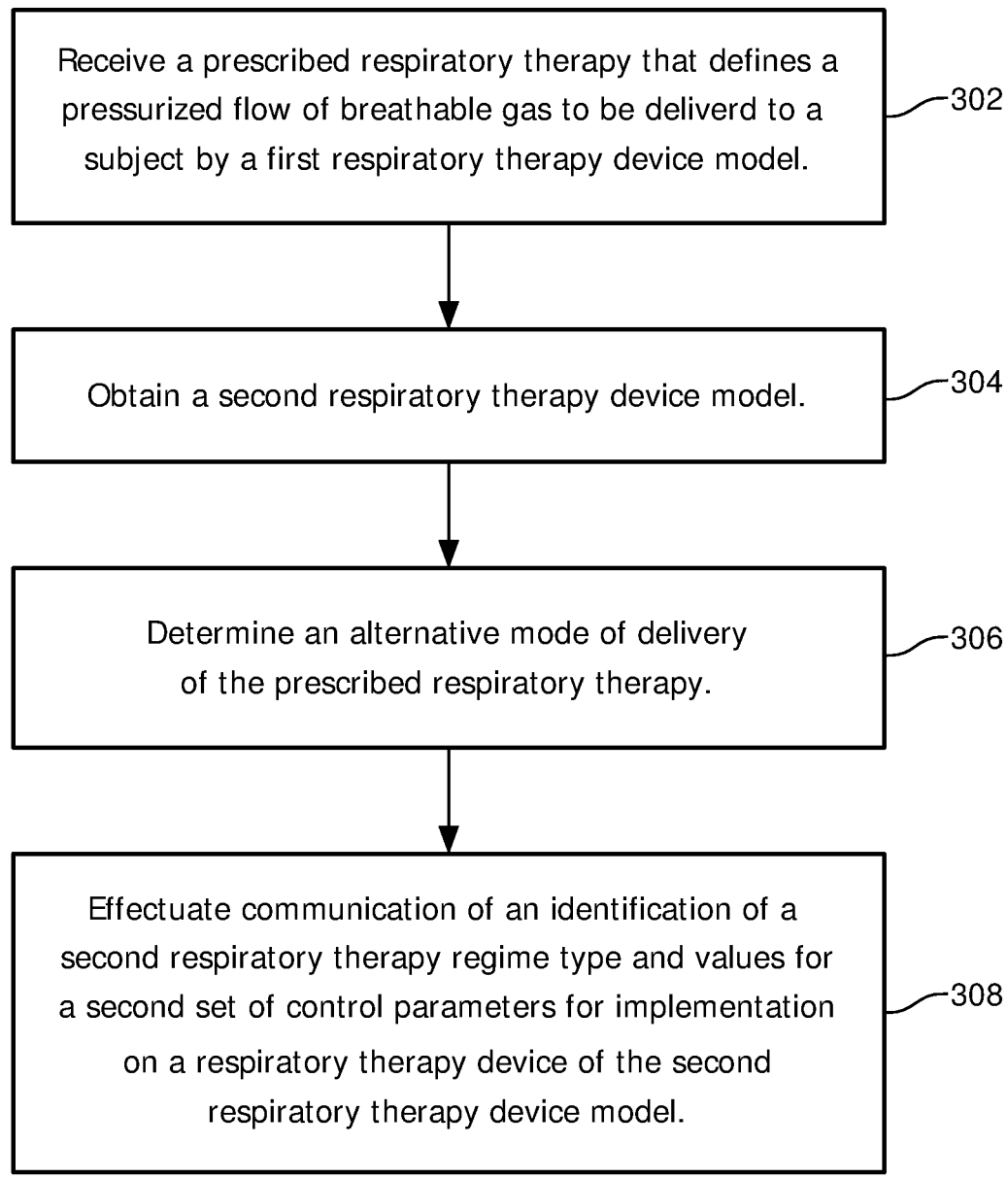
FIG. 3 illustrates a method for determining respiratory therapy control parameters with a parameter translation system.

FIG. 3 illustrates method 300 for determining respiratory therapy control parameters with a parameter translation system. The parameter translation system comprises one or more physical computer processors and/or other components. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting.

In some embodiments, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, a prescribed respiratory therapy for a subject that defines a pressurized flow of breathable gas to be delivered to the subject by a first respiratory therapy device model is received. The prescribed respiratory therapy includes an identification of a first respiratory therapy regime type and values for a first set of control parameters associated with the first therapy regime type. In some embodiments, the prescribed respiratory therapy is received wirelessly via a network. In some embodiments, operation 302 is performed by one or more physical computer processors the same as or similar to processor 20 (shown in FIG. 1 and described herein).

At an operation 304, a second respiratory therapy device model is obtained. In some embodiments, operation 304 is performed by one or more physical computer processors the same as or similar to processor 20 (shown in FIG. 1 and described herein).

At an operation 306, an alternative mode of delivery of the prescribed respiratory therapy to be delivered to the subject by a second respiratory therapy device model different from the first respiratory therapy device model is determined. Determining the alternative mode of delivery of the prescribed respiratory therapy by the second respiratory therapy device model includes determination of an identification of a second respiratory therapy regime type that has a different set of control parameters and/or other information associated with the second therapy regime type, but has been determined to be therapeutically equivalent and/or sufficiently effective. In some embodiments, the second therapy regime is different from the first respiratory therapy regime type but achieves the same and/or similar therapeutic results in a subject relative to the first respiratory therapy regime. Determining the alternative mode of delivery of the prescribed respiratory therapy by the second respiratory therapy device includes identification of the values for the second set of control parameters associated with the second therapy regime type, and/or other information.

In some embodiments, the system further comprises a translation database configured to electronically store information related to the first respiratory therapy device model, the first respiratory therapy regime type, and the values for the first set of control parameters associated with the first therapy regime type; information related to the second respiratory therapy device model, the second respiratory therapy regime type and the values for the second set of control parameters associated with the second therapy regime type; and translation information. The translation information defines relationships between: one or more of the first respiratory therapy device model, the first respiratory therapy regime type, or the values for the first set of control parameters associated with the first therapy regime type, and one or more of the second respiratory therapy device model, the second respiratory therapy regime type, or the values for the second set of control parameters associated with the second therapy regime type. In some embodiments, the translation information stored in the translation database is updatable. In some embodiments, the alternative mode of delivery of the prescribed respiratory therapy to be delivered to the subject by the second respiratory therapy device model is determined based at least in part on the translation information stored in the translation database.

In some embodiments, the system further comprises one or more sensors configured to generate output signals conveying information related to a pressurized flow of breathable gas delivered to the subject by a respiratory therapy device of the first respiratory therapy device model. The alternative mode of delivery of the prescribed respiratory therapy, including the determination of the identification of the second respiratory therapy regime type and the values for the second set of control parameters, to be delivered to the subject by the second respiratory therapy device model may be determined based on the output signals.

In some embodiments, operation 306 is performed by one or more physical computer processors the same as or similar to processor 20 (shown in FIG. 1 and described herein).

At an operation 308, communication of the identification of the second respiratory therapy regime type and the values for the second set of control parameters for implementation on a respiratory therapy device of the second respiratory therapy device model is effectuated. In some embodiments, operation 308 is performed by one or more physical computer processors the same as or similar to processor 20 (shown in FIG. 1 and described herein).

The present invention also contemplates translating these control parameters from one respiratory therapy device to another respiratory therapy device of the same make/model. In which case, the alternative therapy determination component would include the second set of control parameter that this the same as the first set, and no translation between parameters is needed. This allows the features of a first ventilator to be "cloned" to an identical second ventilator without to reenter all of the control parameters into the second device. The present invention further contemplates that if this device-to-device feature translation, in which the first and second devices are the same make/model, is the only desired capability, then the feature of system 20 that have to do with translation the first set of parameters to the second set suitable for the second ventilator, can be eliminated.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A parameter translation system configured to determine respiratory therapy control parameters, the system comprising:
one or more physical computer processors configured by computer readable instructions to:
receive a prescribed respiratory therapy for a subject that defines a pressurized flow of breathable gas to be delivered to the subject by a first respiratory therapy device model, the prescribed respiratory therapy including an identification of a first respiratory therapy regime type and values for a first set of control parameters associated with the first therapy regime type;
obtain a second respiratory therapy device model;
determine an alternative mode of delivery of the prescribed respiratory therapy to be delivered to the subject by the second respiratory therapy device model different from the first respiratory therapy device model, such determination including determination of an identification of a second respiratory therapy regime type different from the first respiratory therapy regime type but substantially therapeutically equivalent to the first therapy regime type, and values for a second set of control parameters associated with the second therapy regime type, wherein the second set of control parameters is different from the first set of control parameters; and
effectuate communication of the identification of the second respiratory therapy regime type and the values for the second set of control parameters for implementation on a respiratory therapy device of the second respiratory therapy device model,
wherein the second set of control parameters includes more or fewer parameters than the first set of control parameters.

2. The system of claim 1, wherein the one or more physical computer processors are configured to receive the prescribed respiratory therapy wirelessly via a network.

3. The system of claim 1, further comprising a translation database configured to electronically store information related to the first respiratory therapy device model, the first respiratory therapy regime type, and the values for the first set of control parameters associated with the first therapy regime type; information related to the second respiratory therapy device model, the second respiratory therapy regime type and the values for the second set of control parameters associated with the second therapy regime type; and translation information that defines relationships between:
one or more of the first respiratory therapy device model, the first respiratory therapy regime type, or the values for the first set of control parameters associated with the first therapy regime type, and
one or more of the second respiratory therapy device model, the second respiratory therapy regime type, or the values for the second set of control parameters associated with the second therapy regime type, wherein the one or more physical computer processors are configured to determine the alternative mode of delivery of the prescribed respiratory therapy to be delivered to the subject by the second respiratory therapy device model based at least in part on the translation information.

4. The system of claim 3, wherein the one or more physical computer processors are configured such that the translation information is updatable.

5. The system of claim 1, further comprising one or more sensors configured to generate output signals conveying information related to a pressurized flow of breathable gas delivered to the subject by a respiratory therapy device of the first respiratory therapy device model, wherein the one or more physical computer processors are configured to determine the alternative mode of delivery of the prescribed respiratory therapy, including the determination of the identification of the second respiratory therapy regime type and the values for the second set of control parameters, to be delivered to the subject by the second respiratory therapy device model based on the output signals.

6. A method for determining respiratory therapy control parameters with a parameter translation system, the system comprising one or more physical computer processors, the method comprising:
receiving, with the one or more physical computer processors, a prescribed respiratory therapy for a subject that defines a pressurized flow of breathable gas to be delivered to the subject by a first respiratory therapy device model, the prescribed respiratory therapy including an identification of a first respiratory therapy regime type and values for a first set of control parameters associated with the first therapy regime type;

obtaining, with the one or more physical computer processors, a second respiratory therapy device model;

determining, with the one or more physical computer processors, an alternative mode of delivery of the prescribed respiratory therapy to be delivered to the subject by the second respiratory therapy device model different from the first respiratory therapy device model, such determination including determination of an identification of a second respiratory therapy regime type different from the first respiratory therapy regime type but substantially therapeutically equivalent to the first therapy regime type, and values for a second set of control parameters associated with the second therapy regime type, wherein the second set of control parameters is different from the first set of control parameters; and effectuating, with the one or more physical computer processors, communication of the identification of the second respiratory therapy regime type and the values for the second set of control parameters for implementation on a respiratory therapy device of the second respiratory therapy device model, wherein the second set of control parameters includes more or fewer parameters than the first set a control parameters.

7. The method of claim 6, further comprising receiving the prescribed respiratory therapy wirelessly via a network.

8. The method of claim 6, wherein the system further comprises a translation database configured to electronically store information related to the first respiratory therapy device model, the first respiratory therapy regime type, and the values for the first set of control parameters associated with the first therapy regime type; information related to the second respiratory therapy device model, the second respiratory therapy regime type and the values for the second set of control parameters associated with the second therapy regime type; and translation information that defines relationships between:

one or more of the first respiratory therapy device model, the first respiratory therapy regime type, or the values for the first set of control parameters associated with the first therapy regime type, and one or more of the second respiratory therapy device model, the second respiratory therapy regime type, or the values for the second set of control parameters associated with the second therapy regime type, wherein the method further comprises determining the alternative mode of delivery of the prescribed respiratory therapy to be delivered to the subject by the second respiratory therapy device model based at least in part on the translation information.

9. The method of claim 8, wherein the translation information is updatable.

10. The method of claim 6, wherein the system further comprises one or more sensors configured to generate output signals conveying information related to the pressurized flow of breathable gas delivered to the subject by a respiratory therapy device of the first respiratory therapy device model, and wherein the method further comprises determining the alternative mode of delivery of the prescribed respiratory therapy, including the determination of the identification of the second respiratory therapy regime type and the values for the second set of control parameters, to be delivered to the subject by the second respiratory therapy device model based on the output signals.

11. A system configured to determine respiratory therapy control parameters, the system comprising:

means for receiving a prescribed respiratory therapy for a subject that defines a pressurized flow of breathable gas to be delivered to the subject by a first respiratory therapy device model, the prescribed respiratory therapy including an identification of a first respiratory therapy regime type and values for a first set of control parameters associated with the first therapy regime type;

means for obtaining a second respiratory therapy device model;

means for determining an alternative mode of delivery of the prescribed respiratory therapy to be delivered to the subject by the second respiratory therapy device model different from the first respiratory therapy device model, such determination including determination of an identification of a second respiratory therapy regime type different from the first respiratory therapy regime type but substantially therapeutically equivalent to the first therapy regime type, and values for a second set of control parameters associated with the second therapy regime type, wherein the second set of control parameters is different from the first set of control parameters; and means for effectuating communication of the identification of the second respiratory therapy regime type and the values for the second set of control parameters for implementation on a respiratory therapy device of the second respiratory therapy device model, wherein the second set of control parameters includes more or fewer parameters than the first set of control parameters.

12. The system of claim 11, wherein the means for receiving is configured to receive the prescribed respiratory therapy wirelessly via a network.

13. The system of claim 11, further comprising means for electronically storing information related to the first respiratory therapy device model, the first respiratory therapy regime type, and the values for the first set of control parameters associated with the first therapy regime type; information related to the second respiratory therapy device model, the second respiratory therapy regime type, and the values for the second set of control parameters associated with the second therapy regime type; and translation information that defines relationships between:

one or more of the first respiratory therapy device model, the first respiratory therapy regime type, or the values for the first set of control parameters associated with the first therapy regime type, and one or more of the second respiratory therapy device model, the second respiratory therapy regime type, or the values for the second set of control parameters associated with the second therapy regime type, wherein the means for determining determines the alternative mode of delivery of the prescribed respiratory therapy to be delivered to the subject by the second respiratory therapy device model based at least in part on the translation information.

14. The system of claim 13, wherein the means for storing information is configured such that the translation information is updatable.

15. The system of claim 11, further comprising means for generating output signals conveying information related to the pressurized flow of breathable gas delivered to the subject by a respiratory therapy device of the first respiratory therapy device model, and wherein the means for determining determines the alternative mode of delivery of the prescribed respiratory therapy, including the determination of the identification of the second respiratory therapy regime type and the values for the second set of control parameters, to be delivered to the subject by the second respiratory therapy device model based on the output signals.

* * * * *